United States Patent [19]

Onoe et al.

[11] Patent Number: 4,740,578

[45] Date of Patent: Apr. 26, 1988

[54] PROCESS FOR PRODUCING POLYTHIOBISPHENOLS AND PROCESS FOR PRODUCING MERCAPTOPHENOLS BY THE HYDROGENOLYSIS OF THE SAME

[75] Inventors: Akira Onoe, Himeji; Masao Kawamura, Akashi; Tadaaki Nishi, Kakogawa; Kenzo Kobayashi, Kakogawa; Masato Yoshikawa, Kakogawa, all of Japan

[73] Assignee: Seitetsu Kagaku Co., Ltd, Hyogo, Japan

[21] Appl. No.: 843,860

[22] Filed: Mar. 24, 1986

[30] Foreign Application Priority Data

Dec. 24, 1984 [JP] Japan .................. 59-279358
Dec. 24, 1984 [JP] Japan .................. 59-279359
Apr. 30, 1985 [JP] Japan .................. 60-94045

[51] Int. Cl.$^4$ .................. C07C 149/36; C07C 148/02
[52] U.S. Cl. .................................. 568/62; 568/23
[58] Field of Search .................. 568/23, 62; 502/222, 502/301, 259, 337

[56] References Cited

U.S. PATENT DOCUMENTS

| | | | |
|---|---|---|---|
| 2,402,614 | 6/1946 | Farlow et al. | 568/62 |
| 2,889,286 | 6/1959 | Faulkner | 502/337 |
| 3,186,956 | 6/1965 | Cabbage | 502/259 |
| 3,479,407 | 11/1969 | Laufer | 568/62 |
| 3,952,064 | 4/1976 | Whalley | 568/64 |
| 4,118,342 | 10/1978 | Debus et al. | 502/222 |

FOREIGN PATENT DOCUMENTS

| | | | |
|---|---|---|---|
| 2021298 | 11/1970 | Fed. Rep. of Germany | 568/23 |
| 1345311 | 1/1974 | United Kingdom . | |

OTHER PUBLICATIONS

Z. Ariyan et al, J. Chem. Soc., 3876 (1962).
E. Hotelling et al, J. Org. Chem., 24, 1598 (1959).
Hackh's Chemical Dictionary, fourth ed., p. 571 (1969), QDSH3.

Primary Examiner—Mary E. Ceperley
Attorney, Agent, or Firm—Wenderoth, Lind & Ponack

[57] ABSTRACT

A process for producing polythiobisphenols which comprises: reacting a phenol having the general formula

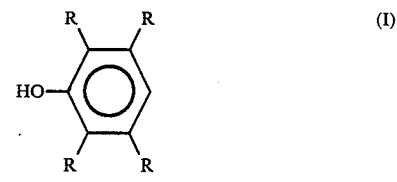

or

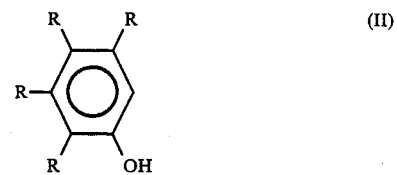

wherein each R independently represents a hydrogen, a halogen or an alkyl, with sulfur monochloride in a polar organic solvent in the presence of a nitrogen-containing organic compound as a catalyst which is selected from the group consisting of tertiary amines, quaternary ammoniums, alkylated acid amides and heteroaromatic compounds, in amounts of about 1–30% by weight based on the amount of the phenol used. As a catalyst, bromine or an alkali metal halide is also usable.

A novel process for producing mercaptophenols by the hydrogenolysis of polythiobisphenols in the presence of a nickel catalyst is also disclosed. Raney nickel catalyst which is in advance poisoned with an organosulfur compound in which the sulfur atom has unshared electron pairs is especially effective as a catalyst.

55 Claims, No Drawings

PROCESS FOR PRODUCING POLYTHIOBISPHENOLS AND PROCESS FOR PRODUCING MERCAPTOPHENOLS BY THE HYDROGENOLYSIS OF THE SAME

This is a continuation-in-part of Ser. No. 739,463, filed May 30, 1985, now abandoned.

The present invention relates to a process for producing polythiobisphenols and a process for producing mercaptophenols by reductive hydrogenation or hydrogenolysis of polythiobisphenols.

Polythiobisphenols are now in use as highly reactive stabilizers as well as intermediates for the production of mercaptophenols, and mercaptophenols are in use as intermediates for the production of medical supplies, agricultural pesticides, color developers and others, or as antioxidants for rubbers and plastics.

It is already known that the reaction of phenols with sulfur monochloride (disulfur dichloride, $S_2Cl_2$) in a solvent to provide dithiobisphenols, and a variety of solvents are claimed to be suitable for use, for example, benzene (Z. S. Ariyan et al., J. Chem. Soc., 3876 (1962), carbon tetrachloride (E. B. Hotelling, J. Org. Chem., 24, 1598 (1959)), petroleum ethers (German Pat. No. 1,145,630), and organic polar solvents having solubility to water of not less than 20 (Japanese Patent Disclosure No. 50-24233). Further according to Ariyan et al. anhydrous hydrogen chloride, ferric chloride, stannic chloride, etc., are effective to accelerate the reaction.

However, these methods have been found to have substantial disadvantages. For example, the methods of Ariyan et al. and of Hotelling produce a large amount of monothiobisphenols and sulfur as byproducts in addition to dithiobisphenols. The use of the Lewis acid as a catalyst as above leaves large portions of the phenol used unreacted, and hence the yield of polythiobisphenol is very low. The catalysis of anhydrous hydrochloric acid is not feasible for industrial production of polythiobisphenols.

It is also disclosed (British Pat. No. 1,345,311) that the reaction of phenols with sulfur monochloride in N,N-dimethylformamide or N-methylpyrrolidone as a solvent in the absence of hydrogen sulfide and a catalyst provides polythiobisphenols in improved yields of about 60–90%. However, according to the prior art, the alkylated acid amides participate in the reaction as an acceptor of the hydrochloric acid generated in the reaction, so that the alkylated acid amide must be used in such amounts that the amide has therein nitrogen atoms equivalent to or more than moles of the phenol used. That is, the alkylated acid amide equivalent to the hydrochloric acid generated in the reaction is converted to the acid amide hydrochloride in the reaction. In fact, the prior process typically uses as much as at least 400 ml of the acid amide per mole of the phenol used, to obtain the corresponding polythiobisphenol in the yield as above stated. Therefore, in this prior method, it is necessary to make the acid amide hydrochloride neutral with an alkali, for example, sodium hydroxide, after the reaction. This results in the production of a large amount of water, and the removal of the water from the reaction mixture is difficult but also deteriorates the process economy. When ammonia is used as an alkali instead of sodium hydroxide, a large amount of ammonium chloride is produced by the neutralization of the acid amide hydrochloride. This makes difficult the recovery and the reuse of the acid amide.

The prior process has further disadvantages in that the process involves the rather violent neutralization reaction of the acid amide in large amounts and hydrochloric acid generated, and accordingly the reaction generates great amounts of neutralization heat. The higher the reaction temperature is, the more vigorous the reaction proceeds, and results in the production of undesired byproducts such as p-chlorophenol and bis(4-hydroxyphenyl)sulfide. Therefore, it is necessary that the reaction is carried out at a low temperature as low as $-10°$ C. to $-40°$ C. to obtain the polythiobisphenol in the yields as called for in the literature, and the process incurs a large cooling cost.

Also it is already known that mercaptophenols are obtainable by hydrogenolysis of polythiobisphenols, and in general, some of the VI or VII group metals in the Periodic Table (U.S. Pat. No. 3,952,064) are known to be useful as a catalyst for the catalytic reduction of sulfides to mercaptophenols. In particular, $MoS_2$ (E. B. Hotelling, J. Org. Chem., 24, 1598 (1959)) and $Co_2S_3$ (U.S. Pat. No. 3,275,694) are known. However, the hydrogenolysis of polythiobisphenols in the presence of these metal sulfide catalysts needs high temperatures and high hydrogen pressures. For instance, the reaction is carried out most preferably at 140° C. under 1800 psi when $MoS_2$ is used, and at 150° C. under 100 kg/cm² when $Co_2S_3$ is used. Furthermore, the $MoS_2$ and $Co_2S_3$ catalysts are readily poisoned by hydrogen sulfide generated as a byproduct in the reaction, so that the catalyst loses its catalytic action in a short period. This means the large consumption of expensive catalysts.

A nickel sulfide catalyst is also known to be effective for hydrogenation of acyclic or alicyclic polysulfides to the corresponding thiols (U.S. Pat. No. 2,402,614). The nickel sulfide catalyst is prepared, for example, by reacting nickel chloride with sodium sulfide and sulfur in water, and is used, for example, as a paste in dioxane. However, as it is well known that acyclic and alicyclic sulfides are in many aspects different in chemical reactivity, especially in the hydrogenation reaction, from aromatic polysulfides; all the catalysts effective for the hydrogenation of aliphatic sulfides are not applicable to the hydrogenation reaction of aromatic polysulfides. In fact, the nickel sulfide catalyst has been found by the inventors to be substantially ineffective for the hydrogenation of polythiobisphenols to the corresponding mercaptophenols. Other methods are also described in the prior art to prepare the metal sulfide catalyst. For instance, a metal is treated with hydrogen sulfide, sulfur or carbon disulfide. However, the resulting catalyst has been also found substantially ineffective for the hydrogenation of aromatic polysulfides. Therefore, the methods using the above metal sulfide catalysts are not suitable for industrial scale production of mercaptophenols by the hydrogenolysis of polythiobisphenols.

It is apparently very important from the viewpoint of industrial production of mercaptophenols that the hydrogenolysis reaction can be carried out under mild conditions to provide mercaptophenols in high yields, with the use of small amounts of a less expensive catalyst which stands the use over along period and the reuse. However, no such a catalyst is known to date.

The present inventors have therefore made extensive studies on processes for producing polythiobisphenols, and found out that the specified catalysts accelerate the reaction of phenols with sulfur monochloride in an organic polar solvent to provide polythiobisphenols in high yields with a minimum production of undesired monothiobisphenols. The present inventors have made further studies on the reductive hydrogenation or hydrogenolysis reaction of polythiobisphenols to the corresponding mercaptophenols, and found out that the reaction can be carried out under a lower hydrogen pressure in the presence of nickel catalysts to provide the corresponding mercaptophenols in high yields.

Therefore, an object of the present invention is to provide a process for producing polythiobisphenols by the reaction of phenols with sulfur monochloride in the presence of a novel catalyst.

A further object of the present invention is to provide a novel process for producing mercaptophenols by the hydrogenolysis of polythiobisphenols in the presence of a nickel catalyst in higher yields than any other process ever known.

A still further object of the present invention is to provide a process for producing polythiobisphenols and a process for producing mercaptophenols by the hydrogenolysis of the same which are simple in operations and mild in reaction conditions so as to be suitable for industrial production of polythiobisphenols and mercaptophenols.

According to the present invention, a process for producing polythiobisphenols is provided, the process comprising:

reacting a phenol having the general formula

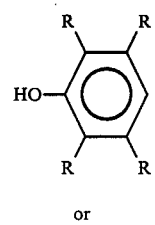
(I)

or

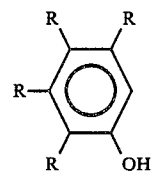
(II)

wherein each R independently represents a hydrogen, a halogen or an alkyl, with sulfur monochloride in a polar organic solvent in the presence of a nitrogen-containing organic compound as a catalyst which is selected from the group consisting of tertiary amines, quaternary ammoniums, alkylated acid amides and heteroaromatic compounds, in amounts of about 1–30% by weight based on the amount of the phenol used, thereby to provide the polythiobisphenol having the general formula

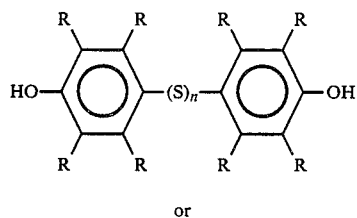
(III)

or

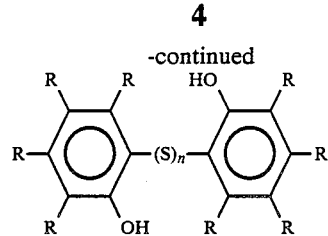
(IV)

wherein R is the same as above, and n is an integer of 2–4.

Further according to the present invention, another process for producing polythiobisphenols is provided, the process comprising:

reacting the phenol as above with sulfur monochloride in a polar organic solvent in the presence of bromine or an alkali metal halide, in amounts of about 200–2000 ppm based on the amount of sulfurmonochloride.

Still further according to the present invention, a novel process for producing mercaptophenols is provided. The process comprises:

reducing polythiobisphenols having the general formula (III) or (IV) as above, with hydrogen in the presence of a nickel catalyst, thereby to provide the mercaptophenol having the general formula

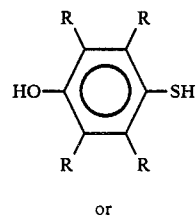
(V)

or

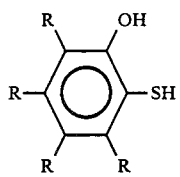
(VI)

wherein R is the same as above.

At first, the process for production of polythiobisphenols according to the invention is described.

The phenol used as the starting material in the process of the invention is represented by the general formula

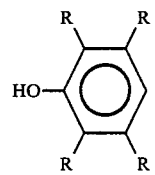
(I)

or

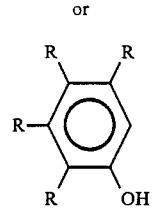
(II)

That is, the phenol should have no substituent at least at the para position or at least at one of the ortho positions to the hydroxyl group, since a first phenol is united with a second phenol at the para or ortho positions to the hydroxyl via polysulfide linkage. The substituents R's are independently hydrogens, halogens or alkyls which have preferably 1 to 4 carbons. Therefore, the phenol preferably used includes, for example, phenol, o-cresol, o-chlorophenol, 2,6-dimethylphenol, 2,6-diisopropylphenol, 2,6-di-tertiary butylphenol, 2,6-dichlorophenol, 2,3,5,6-tetramethylphenol, p-cresol, p-isopropylphenol, p-tertiary butylphenol, p-chlorophenol and p-fluorophenol.

The reaction of the phenol with sulfur monochloride is carried out in a polar organic solvent, such as aliphatic ethers, alicyclic ethers, alkyleneglycol dialkylethers, polyalkyleneglycol dialkylethers, alkyleneglycol monoether monoester, polyalkyleneglycol monoether monoester, aliphatic carboxylic acid alkylesters, or the like. In general, the more polar a solvent is, the higher the selectivity of the reaction and the yield of polythiobisphenol are. The most preferred solvents are, for example, diethylether, dioxane, dimethoxyethane, ethylglycol acetate (ethyleneglycol monoethylether monoacetate), ethyl acetate and the like. The solvent is normally used in amounts of about 2–10 times as much as the weight of the phenol used, and preferably about 3–8 times as much as the amount of the phenol used.

The reaction according to the invention is carried out in the presence of a catalyst. The first group of the catalyst is a nitrogen-containing organic compound which is selected from the group consisting of tertiary amines, preferably aliphatic and alicyclic tertiary amines, quaternary ammoniums, alkylated acid amides and heteroaromatic compounds. Preferred catalysts are, for example, tertiary amines such as trimethylamine, triethylamine, triethylenediamine or tetramethylethylenediamine, organic quaternary ammoniums such as trialkylarylammonium halide, e.g., trimethylbenzylammonium chloride and triethylbenzylammonium chloride or tetraalkylammonium halide, e.g., tetramethylammonium chloride, alkylated acid amides such as N,N-dialkylformamide, e.g., N,N-dimethylformamide, N,N-dialkylacetamide, e.g., N,N-dimethylacetamide or N-alkylpyrrolidone, e.g., N-methylpyrrolidone, and heteroaromatic compounds such as pyridine, 2-chloropyridine, α-picoline or β-picoline.

The above catalyst is normally used in amounts of about 1–30% by weight based on the amount of the phenol used. The use of less than about 1% by weight based on the phenol used is lacking in effective catalysis. On the other hand, the use of more than about 30% results in the increase in the undesired byproduct as set forth hereinbefore and the decrease in the yield of the polythiobisphenol. Preferably the amount of the catalyst is from about 2–20% by weight, and most preferably from about 3–12% by weight based on the amount of the phenol used. In addition, the use of too much of the catalyst is disadvantageous from a point of view of process economy, for instance, the separation cost for the acid amide hydrochloride produced in large amounts is additionally imposesd on the process as well as the catalyst expenses increase.

In the process of the invention, however, the nitrogen-containing compound as the catalyst may accelerate the elimination of hydrogen chloride generated in the reaction of the phenol and sulfur monochloride.

The use of only a small amount of acid amide catalyst is an important feature of the invention, because substantially no neutralization heat is generated in the reaction, and therefore the reaction can be carried out under milder conditions. For instance, the reaction can be carried out at a much higher and accordingly more practical temperature such as about 5° C. to provide the polythiobisphenol in high yields with a minimum generation of byproducts. Further there is no need to separate the acid amide hydrochloride if generated in the reaction since the amount thereof is very small. These advantages make the production cost of the polythiobisphenol according to the invention much less expensive compared with the prior process using a large excess amounts of acid amides as a solvent as described hereinbefore.

The second group of the catalyst is a halogen, especially bromine, and an alkali metal halide such as lithium chloride, lithium bromide, lithium iodide or potassium iodide. The catalyst in the second group is normally used in amounts of about 200–2000 ppm based on the amount of sulfur monochloride used. The use of less than about 200 ppm based on the amount of sulfur monochloride used is insufficient for practical production of polythiobisphenols, while the use of more than about 2000 ppm is disadvantageous from a point of view of process economy.

The catalysis of bromine or alkali metal halide may be based on the formation of ClSSX (X: Br or I) by the reaction of sulfur monochloride with MX or $X_2$ (M: an alkali metal such as Li, Na or K; X: a halogen such as Br or I), and the resultant ClSSX reacts with a phenol to form a ClSS-substituted phenol with the simultaneous elimination of hydrogen halide (HX). The hydrogen halide thus formed then reacts with sulfur monochloride to form hydrogen chloride and ClSSX. The reaction scheme is presented below. The bromine or iodine atom in the MX or $X_2$ as the catalyst is likely to be recirculated via HX, i.e., hydrogen bromide or iodide in the reaction system.

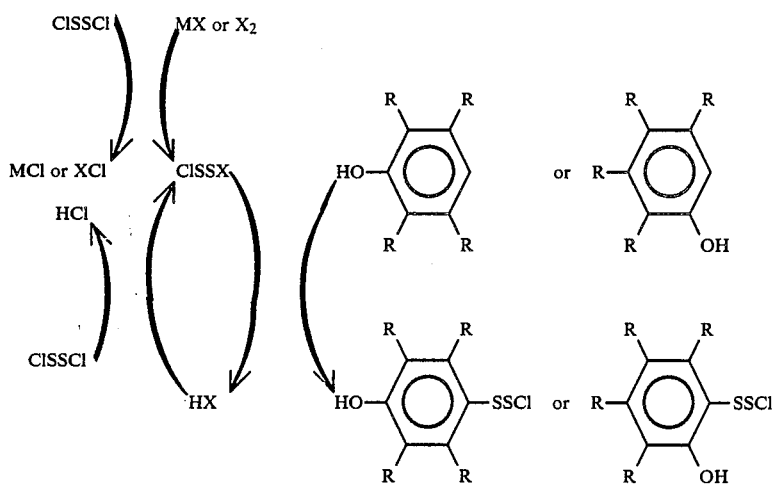

The reaction of the phenol with sulfur monochloride in the presence of the catalyst according to the invention provides the polythiobisphenol having the general formula

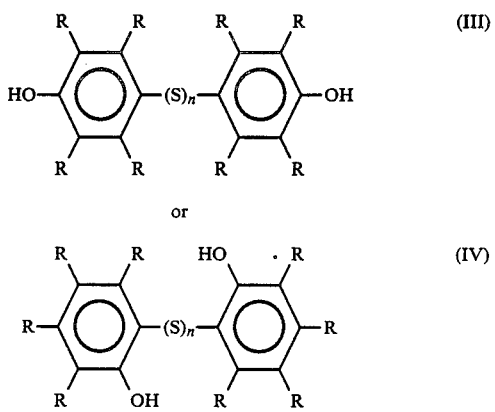

wherein R is the same as above, and n is an integer of 2–4.

The main products of the reaction of the invention are di- and/or trithiobisphenols. The selectivity of the reaction is mainly dependent upon the substituents on a phenol aromatic ring. The mechanism of the reaction of the invention is not fully clear, however, when the both sides of the carbon atom as the reaction site are substituted, the main product is trithiobisphenols possibly on account of steric effects concerned.

A preferred embodiment of the present process for producing polythiobisphenols is now presented. At first, 1 mole of phenol is dissolved in an ethylglycol acetate which contains a catalyst therein, for instance, benzyltriethylammonium chloride or pyridine. Then sulfur monochloride in amounts of from 0.5 to 0.75 moles is added dropwise to the solution at temperatures of about −20° C. to 50° C., preferably about −20° C. to 30° C., most preferably about −10° C. to 10° C., while cooling the solution. When the reaction temperature is lower than about −20° C., the reaction proceeds too slowly, and when the reaction temperature is higher than about 50° C., undesired side reactions take place to make the yield of polythiobisphenol small.

The resultant reaction mixture is a yellow or pale yellow homogeneous solution, and the polythiobisphenol therein is separable by various methods. In a typical method, the solvent is removed by evaporation to leave an oily substance which contains crude polythiobisphenols together with monothiobisphenols as byproducts. Then nearly the same amount of benzene as the oily substance is added thereto, and the mixture is stirred at the room temperature until the crystallization of the polythiobisphenol begins. Then byproducts soluble in benzene are removed by filtration from the resultant paste-like material to provide polythiobisphenols in yields of about 65–90%. The thus obtained polythiobisphenols may be further purified, when necessary, by recrystallization in benzene or benzene/petroleum ethers.

When the reaction mixture is soluble in water, the reaction mixture after the reaction may be poured into water, the resulting oily substance is separated, and low boiling point components are evaporated at temperatures of about 100°–110° C. from the oily substance. The crystallization in the same manner as above provides polythiobisphenols.

Further according to the present invention, a novel process for producing mercaptophenols is provided. The process is now described.

The process comprises reducing the polythiobisphenol having the general formula of (III) or (IV) as mentioned hereinbefore with hydrogen in the presence of a nickel catalyst, thereby to provide the mercaptophenol having the general formula

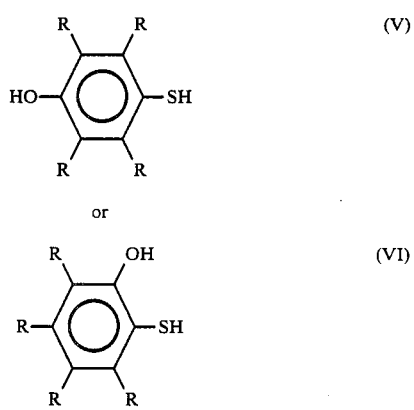

wherein R is the same as above.

Therefore, the polythiobisphenol usable includes, for example, bis(4-hydroxyphenyl)polysulfide, bis(3-methyl-4-hydroxyphenyl)polysulfide, bis(2,6-dimethyl-4-hydroxyphenyl)polysulfide, bis(2,6-diisopropyl-4-hydroxyphenyl)polysulfide, bis(2,6-di-tertiary butyl-4-hydroxyphenyl)polysulfide, bis(2,3,5,6-tetramethyl-4-hydroxyphenyl)polysulfide, bis(2-hydroxy-5-methylphenyl)polysulfide, bis(2-hydroxy-5-isopropylphenyl)polysulfide, bis(2-hydroxy-5-tertiary butylphenyl)polysulfide, and the like.

In this reductive hydrogenation or hydrogenolysis, dithio- and/or trithiobisphenols are preferably used as the polythiobisphenol. A molecule of dithiobisphenol provides two molecules of mercaptophenols, and a molecule of trithiobisphenol provides two molecules of mercaptophenols and a molecule of hydrogen sulfide. A molecule of tetrathiobisphenol provides two molecules of mercaptophenols and two molecules of hydrogen sulfide.

The nickel catalyst usable in the invention includes Raney nickel catalyst and the nickel supported on diatomaceous earth. The Raney nickel catalyst includes a so-called stabilized Raney nickel catalyst as well as Raney nickel catalyst usually known. The nickel/diatomaceous earth catalyst includes a stabilized nickel catalyst and a so-called sulfur-resistant nickel catalyst. The stabilized Raney nickel catalyst has a coating of nickel oxide on the surface and is stable in the air. However, in a reaction system of temperatures not less than about 100° C., the coating is dissolved in a solvent used, and the effects as a usual Raney nickel catalyst.

According to the present invention, the Raney nickel catalyst is preferably in advance poisoned by organosulfur compounds. Unexpectedly the use of the poisoned Raney nickel catalyst makes the reaction rate faster than the use of nonpoisoned catalyst, on the contrary to the conventional well-known catalysis of Raney nickel catalysts.

The catalyst poison usable in the invention is an organosulfur compound in which the sulfur atom has unshared electron pairs, among which are, for example, aliphatic mercaptanes, aliphatic mercaptoalcohol, aromatic mercaptanes and heteroaromatic sulfur compounds. Preferred examples are alkyl mercaptanes in which the alkyl has 2-24 carbons, preferably 4-20 carbons, such as butyl mercaptane, octyl mercaptane, dodecyl mercaptane, hexadecyl mercaptane or octadecyl mercaptane, aliphatic mercaptoalcohols in which the alkylene has 2-20 carbons such as 2-mercaptoethanol, 3-mercaptopropanol, 2-hydroxyhexane-1-thiol, 2-hydroxyoctane-1-thiol or 2-hydroxydodecane-1-thiol, aromatic mercaptanes such as thiophenol, 2-mercaptophenol, 4-mercaptophenol, thioanisole or benzyl mercaptane, and heteroaromatic sulfur compounds such as thiophene, 2-methylthiophene, 4-methylthiophene, thiolane or 1,4-dithiane.

The poisoning of nickel catalyst is usually carried out by heating the nickel catalyst in the organosulfur compound at temperatures not less than 50° C., preferably not less than 100° C. The period of time for the poisoning is somewhat dependent upon the nickel catalyst and the organosulfur compound used, but is usually from a few minutes to a few hours. As another method, the nickel catalyst may be heated in an atmosphere which contains vapor of the catalyst poison at temperatures preferably not less than 100° C. in a sealed vessel. The thus poisoned nickel catalyst increases the reaction rate by several tens to several hundreds of percent.

It is still not clear why the poisoned nickel catalyst accelerates the hydrogenolysis of the polythiobisphenol, however, the poisoning of nickel catalyst with hydrogen sulfide in fact makes the catalyst ineffective for the hydrogenolysis, i.e., the poisoning in the conventional meaning results. Therefore, it is likely that the catalyst in advance poisoned with the organosulfur compound as hereinbefore mentioned is prevented from being poisoned in the conventional meaning by hydrogen sulfide which is generated in the reaction of the present hydrogenolysis reaction.

The nickel catalyst, which is either nonpoisoned or poisoned, is used preferably in amounts of about 1-30%, most preferably about 5-10% by weight, based on the amount of the polythiobisphenol used. When the amount of the catalyst is less than about 1% based on the weight of the polythiobisphenol used, the hydrogenolysis is insufficient for practical production of mercaptophenols. The use of more than about 30% is unfeasible mainly from the viewpoint of process economy.

The reductive hydrogenation of the polythiobisphenol is carried out in an organic solvent. The solvent usable is not restricted to any specific one, so far as the solvent is known to be usable in reduction reactions with conventional nickel catalysts. Aliphatic alcohols, aliphatic and alicyclic ethers, aliphatic and aromatic hydrocarbons are usually used. Among these solvents, aromatic hydrocarbons are most preferred such as benzene, toluene or xylene, since the hydrogenolysis reaction proceeds in these aromatic solvents more rapidly than in the others.

The reaction temperature is preferably from about 120° C. to about 180° C., and most preferably 140° C. to about 160° C. When the reaction is carried out at too low a temperature, the reaction rate is unfeasibly slow, and when the reaction is carried out at too high a temperature, e.g., 200° C., the reaction products, i.e., mercaptophenols tend to decompose so that the yield decreases.

The reductive hydrogenation of the polythiobisphenol is carried out usually at pressures not less than 5 kg/cm$^2$, and preferably not less than 10 kg/cm$^2$. However, the pressure up to about 50 kg/cm$^2$, preferably up to about 30 kg/cm$^2$ is sufficient to obtain high yields of mercaptophenols according to the invention.

A preferable embodiment of the reductive hydrogenation of the polythiobisphenol is described. Raney nickel is admixed with octyl mercaptane and the mixture is heated at about 100° C. for 2 hours. Then the water and the octyl mercaptane in the mixture are removed by distillation, and then washed with toluene, to provide a poisoned Raney nickel catalyst preferably usable in the present invention.

A polythiobisphenol, toluene and the poisoned nickel catalyst are placed in an autoclave provided with a magnetic stirrer. The inside of the autoclave is replaced by nitrogen, and then the nitrogen is replaced by hydrogen. The hydrogen pressure is preferably 5 kg/cm$^2$ or more, and most preferably not less than 10 kg/cm$^2$. Then the reactive mixture is heated to about 150°-160° C. to start the reaction. As the hydrogenolysis reaction proceeds, the hydrogen pressure inside the autoclave decreases, and therefore, hydrogen is continuously or intermittently added into the autoclave. Usually about 5-20 hours, the consumption of the hydrogen ceases, and then the reaction mixture is allowed to be cooled, and then the catalyst is removed from the reaction mixture by filtration. After the toluene is removed from the reaction mixture by distillation, the vacuum distillation of the residue provides 4-mercaptophenol in reduction yields of 90–100%. When necessary, the rectification by a rectifying column of the product provides highly purified 4-mercaptophenol.

The present invention will be more clearly understood by reference to the following examples, which however are intended only to illustrate the invention and are not to be construed as limiting the scope of the invention.

In the following examples of the production of polythiobisphenols according to the process of the invention, the polythiobisphenol produced was analyzed in the method described below. Amounts sampled or the whole of the reaction mixture were reduced quantitatively with the use of zinc powder and concentrated hydrochloric acid to convert the polythiobisphenols to the corresponding mercaptophenols (Japanese Patent Publication No. 49-10943). Then the mercaptophenol was subjected to gas chromatographic analysis to find the yield of the polythiobisphenols produced by the reaction of phenol and sulfur monochloride.

EXAMPLE 1

In a 1000 ml capacity four neck flask provided with a stirrer, a thermometer, a dropping funnel, an inlet tube for nitrogen, a drying tube and a reflux condenser were placed 500 g of ethylglycol acetate. Then 94.1 g (1 mole) of phenol was dissolved in the solvent, and 5 g of N,N-dimethylformamide was added thereto.

The inside of the flask was replaced by nitrogen, and then 74.3 g (0.55 mole) of sulfur monochloride was dropwise added to the mixture with stirring and cooling with ice water to keep the reaction mixture at temperatures of about 5° C. After the reaction for 4 hours at about 5° C., the reaction mixture was gradually heated and then the ethylglycol acetate was removed therefrom by vacuum distillation to provide 138.5 g of an oily substance which contained crude polythiobisphenols and monothiobisphenols as byproducts.

A small portion of the oily substance thus obtained is sampled, 20 g of toluene was added thereto and dissolved therein by heating. Then, zinc powder and 35% hydrochloric acid were added to the mixture and the quantitative reduction of the oily substance was carried out. The resultant organic layer was separated from the reaction mixture, and the resultant mercaptophenol therein was determined by the gas chromatography internal standard method. Based on this result, the ratio of the phenol initially used to the amount of the phenol consumed for the production of polythiobisphenols, i.e., the yield of the polythiobisphenol, was found 81%.

In the same manner as above, phenol was reacted with sulfur monochloride in the presence of N,N-dimethylformamide in varied amounts. The amount of N,N-dimethylformamide used and the resultant yield of polythiobisphenol are shown in Table 1.

TABLE 1

| Amounts of Catalysts (% by weight)[1] | Yield of Polythiobisphenols (%) |
| --- | --- |
| 0[2] | 60 |
| 1.3 | 71 |
| 2.7 | 73 |
| 5.3 | 77 |
| 10.6 | 79 |
| 21.3 | 77 |
| 25.6 | 70 |

[1]Based on the weight of phenol used.
[2]See Comparative Example 1.

The use of N,N-dimethylacetamide instead of N,N-dimethylformamide provided the results similar to those obtained with N,N-dimethylformamide.

An amount of 50 g of Raney nickel (Kawaken Fine Chemical K.K.) was mixed with 50 g of octyl mercaptane, and the mixture was heated at 100° C. for 2 hours with stirring. Then the water and the mercaptane were removed by vacuum distillation. To the resultant residue was added 50 g of toluene, and then the toluene was removed by filtration from the mixture to provide 38 g of poisoned Raney nickel catalyst.

An amount of 83.1 g of the oily substance which contained the polythiobisphenol (corresponding to 81% of 0.6 moles of phenol) and 60 g of toluene were placed together with 6.3 g of the poisoned Raney nickel catalyst in a 300 ml capacity autoclave. The inside of the autoclave was replaced by nitrogen, and then the nitrogen was replaced by hydrogen of a pressure of 15 kg/cm$^2$. The mixture was then heated to 150° C. to start the reaction, when the inside was under a pressure of 20 kg/cm$^2$. During the reaction, every time the inside hydrogen pressure decreased to 18 kg/cm$^2$, hydrogen was supplied into the autoclave to pressurize the inside at 20 kg/cm$^2$.

After the reaction at 150° C. for 8 hours when the consumtion of hydrogen in the autoclave ceased, the autoclave was allowed to cool, the pressure inside thereof was released, and the reaction mixture was taken out of the autoclave. The resultant reaction mixture was filtered to remove the catalyst therefrom and then the toluene was removed by vacuum distillation to provide 60.1 g of 4-mercaptophenol (bp. 115°–116° C./5 mmHg). By gas chromatographic analysis, the 4-mercaptophenol was found 97% purity. Therefore, the reduction yield calculated was 95%.

The same Raney nickel as the above were poisoned with various organosulfur compounds in the same manner as above. The hydrogenolysis of polythiobisphenol was carried out in the same manner as above at a temperature of 150° C. The rate of the hydrogen consumption when the poisoned catalyst was used compared with the hydrogen consumption when the nonpoisoned catalyst was used are shown in Table 2.

TABLE 2

| Organosulfur compounds | Rates of Hydrogen Consumption |
| --- | --- |
| octyl mercaptane | 2.5 |
| dodecyl mercaptane | 1.9 |
| 2-mercaptoethanol | 1.7 |
| thiophenol | 1.5 |
| 4-mercaptophenol | 1.3 |
| thiophene | 1.3 |
| sulfolane* | 1.0 |
| (nonpoisoned) | 1.0 |

*Sulfolane has no unshared electron pairs.

COMPARATIVE EXAMPLE 1

In the production of polythiobisphenol, the same procedure as EXAMPLE 1 was repeated except that N,N-dimethylformamide was not used. After the addition of sulfur monochloride, an induction period of 2–3 hours was observed, and thereafter the reaction began, and proceeded rather violently. After another 4 hours, the reaction mixture was gradually heated, and then the ethylglycol acetate was removed by vacuum distillation to provide 138.2 g of an oily substance.

The reduction of the oily substance with zinc and hydrochloric acid was carried out, and the reaction product was analyzed in the same manner as in EXAMPLE 1. The yield of the polythiobisphenol was found to be 60%.

COMPARATIVE EXAMPLE 2

A nickel sulfide hydrogenation catalyst was prepared in a manner suggested by U.S. Pat. No. 2,402,614 to Farlow et al.

In a 500 ml capacity four neck flask provided with a stirrer, a thermometer, a dropping funnel, an inlet tube for nitrogen and a reflux condenser were placed 150 ml of water, 24 g of sodium sulfide nonahydrate and 64 g of sulfur, and heated at 50° C. with stirring under nitrogen atmosphere. Almost all of the sulfur was found remained undissolved in water.

An aqueous solution of 23.8 g of nickel chloride hexahydrate in 170 ml of water was added dropwise over about 1.5 hours to the above solution of sodium sulfide at a temperature of 50° C. under nitrogen atmosphere. The sulfur became dark but remained undissolved. The mixture was further stirred for another 1 hour.

Thereafter the reaction mixture was filtered, and the solid was twice washed each with 200 ml of water and then thrice each with 100 ml of dioxane, to provide 101 g of paste-like black precipitates. The calculated amount of nickel sulfide in the precipitate was 9.1 g and the remainders were unreacted sulfur, water, etc. The paste-like precipitate was stored until it was used.

In the same manner as in Example 1, 83.1 g of the oily substance as described hereinbefore which contained the polythiobisphenol (corresponding to 81% of 0.6 moles of phenol) and 60 g of dioxane were placed together with 8.3 g of the pastelike catalyst, and the hydrogenation was carried out at 150° C. for 8 hours under hydrogen of a pressure of 20 kg/cm$^2$. The reduction yield of 4-mercaptophenol was calculated to be 12.8%/0/81, i.e., 15.8%.

COMPARATIVE EXAMPLE 3

A further nickel sulfide hydrogenation catalyst was prepared in a manner suggested by Farlow et al.

An amount of 50 g of the same Raney nickel as used in Example 1 was first washed with methanol and secondly with toluene, and then was immersed in 300 ml of toluene. Then, the Raney nickel in toluene was placed in a 500 ml capacity four neck flask provided with a stirrer, a thermometer, an inlet tube for hydrogen sulfide gas and a reflux condenser. The toluene was refluxed while hydrogen sulfide gas was intoduced into the flask at a rate of 120-160 ml/min. for 2 hours to sulfidate the Raney nickel. The total amount of hydrogen sulfide introduced was 29 g.

After cooling, nitrogen was bubbled into the reaction mixture to remove the hydrogen sulfide dissolved therein, and then the reaction mixture was washed with toluene until the filtrate bacame colorless and transparent. The resultant sulfidated nickel catalyst was stored in toluene until it was used.

In the same manner as in Example 1, 83.1 g of the oily substance as described hereinbefore which contained the polythiobisphenol (corresponding to 81% of 0.6 moles of phenol) and 60 g of toluene were placed together with 8.3 g of the catalyst, and the hydrogenation was carried out at 150° C. for 8 hours under a 20 kg/cm$^2$ hydrogen pressure. The reduction yield of 4-mercaptophenol was calculated to be 12.4%/0/81. i.e., 15.3%.

COMPARATIVE EXAMPLE 4

This example is to compare the process of British Pat. No. 1,345,311 with the process of the invention.

In a 1000 ml capacity four neck flask provided with a stirrer, a thermometer, a dropping funnel, a nitrogen inlet tube, a drying tube and a reflux condenser were placed a solution of 94.1 g (1 mole) of phenol in 400 ml of N,N-dimethylformamide (401% by weight based on the phenol).

The inside of the flask was replaced by nitrogen, and then 67.5 g (0.50 mole) of sulfur monochloride in 150 ml of benzene was dropwise added to the mixture over about 4 hours with stirring at a temperature of about −20° C. After the addition of the sulfur monochloride, the reaction mixture was heated gradually to room temperature, followed by stirring for 2 hours.

A small portion of the reaction mixture was sampled, and was subjected to the quantitative reduction reaction by the use of zinc and hydrochloric acid in the same manner as in Example 1. By quantitative analysis of the resultant mercaptophenol by gas chromatography, the yield of the polythiobisphenol was found 68.7%.

However, when the reaction was carried out in the same manner as above except the reaction temperature of −5° C., the yield of the polythiobisphenol was found to be 61.6%.

EXAMPLE 2

In the production of polythiobisphenol, the same procedure as EXAMPLE 1 was repeated except that diethylether and triethylamine were used instead of ethylglycol acetate and N,N-dimethylformamide as a solvent and a catalyst, respectively. 138.6 g of oily substance was obtained. The same analysis as EXAMPLE 1 with this substance proved that the yield of the polythiobisphenol was 73%.

An amount of 83.2 g of the above oily substance which contained the polythiobisphenol (corresponding to 73% of 0.6 moles of phenol) and 60 g of toluene were placed together with 6.3 g of the poisoned Raney nickel catalyst prepared in EXAMPLE 1 in a 300 ml capacity autoclave. Then the reaction was carried out in the same manner as in EXAMPLE 1, to provide 54.5 g of 4-mercaptophenol. By gas chromatographic analysis, the 4-mercaptophenol was found to have 96% purity. Thus the reduction yield was found to be 95%.

EXAMPLE 3

In the production of polythiobisphenol, the same procedure as EXAMPLE 1 was repeated except that ethyl acetate and pyridine were used instead of ethylglycol acetate and N,N-dimethylformamide as a solvent and a catalyst, respectively. An oily substance was obtained in an amount of 138.1 g. By the same analysis as EXAMPLE 1 with this substance, the yield of the polythiobisphenol was found 76%.

The hydrogenolysis of 82.9 of the above oily substance which contained the polythiobisphenol (corresponding to 76% of 0.6 moles of phenol) with the use of 6.3 g of the poisoned Raney nickel catalyst in the same manner as in EXAMPLE 1 provided 56.5 g of 4-mercaptophenol. The purity was found to be 97%, and thus the reduction yield was found to be 95%.

EXAMPLE 4

In the production of polythiobisphenol, the same procedure as EXAMPLE 1 was repeated except that dimethoxyethane and trimethylbenzylammonium chloride were used instead of ethylglycol acetate and N,N-dimethylformamide as a solvent and a catalyst, respectively. 138.5 g of an oily substance was obtained. The same analysis as in EXAMPLE 1 with this substance showed that the yield of the polythiobisphenol was 80%.

An amount of 20 g of stabilized Raney nickel (Nikko Rika K.K.) was mixed with 20 g of octyl mercaptane, and the mixture was heated at 100° C. for 2 hours with stirring. Then the mercaptane were removed by vacuum distillation. To the resultant residue was added 30 g of toluene, and then the toluene was removed by filtration from the mixture to provide 23.5 g of poisoned Raney nickel catalyst.

The hydrogenolysis of 83.1 g of the above oily substance which contained the polythiobisphenol (corresponding to 80% of 0.6 moles of phenol) was carried out in the same manner as in EXAMPLE 1 at 150° C. for 10 hours with the use of 6.3 g of the above poisoned Raney nickel catalyst, to provide 60.2 g of 4-mercaptophenol, which was found to have 97% purity. Then, the calculated reduction yield was found to be 96%.

EXAMPLE 5

The same procedure as EXAMPLE 1 was repeated except that ethyl acetate and bromine were used instead of ethylglycol acetate and N,N-dimethylformamide as a solvent and catalyst, respectively. This reaction provided 137.6 g of an oily substance. The same analysis as EXAMPLE 1 with this substance proved that the yield of the polythiobisphenol was 74%.

The hydrogenolysis of 82.6 g of the above oily substance which contained the polythiobisphenol (corresponding to 74% of 0.6 moles of phenol) was carried out in the same manner as in EXAMPLE 1 at 150° C. for 10 hours with the use of 6.3 g of the poisoned Raney nickel catalyst prepared in EXAMPLE 4, to provide 55.4 g of 4-mercaptophenol, which was found to have 96% purity. Thus the reduction yield was found to be 95%.

COMPARATIVE EXAMPLE 5

The same procedure as EXAMPLE 5 was repeated except that bromine as a catalyst was not used. After the addition of sulfur monochloride, an induction period of 2-3 hours was observed, and thereafter the reaction began and proceeded rather violently. After another 4 hours, the reaction mixture was gradually heated and then the ethyl acetate was removed by vacuum distillation to provide 137.4 g of an oily substance. The same analysis as EXAMPLE 1 with this substancse proved that the yield of the polythiobisphenol was 58%.

EXAMPLE 6

An amount of 50 g of Raney nickel (Kawaken Fine Chemical K.K.) was mixed with 50 g of dodecyl mercaptane, and the mixture was heated at 100° C. for 2 hours with stirring. Then the water and the mercaptane were removed from the mixture by vaccum distillation. To the resultant residue was added 50 g of toluene, and then the toluene was removed by filtration from the mixture to provide 38 g of poisoned Raney nickel catalyst.

The hydrogenolysis of 83.1 g of the oily substance obtained in EXAMPLE 1 which contained the polythiobisphenol (corresponding to 81% of 0.6 moles of phenol) was carried out in the same manner as in EXAMPLE 1 at 150° C. for 10 hours with the use of 6.3 g of the above poisoned Raney nickel catalyst, to provide 60.0 g of 4-mercaptophenol, which was found to have 97% purity. Then, the calculated reduction yield was found to be 95%.

EXAMPLE 7

An amount of 50 g of Raney nickel (Kawaken Fine Chemical K.K.) was mixed with 50 g of thiophene, and the mixture was heated at 60° C. for 3 hours with stirring. After cooling, the mixture was filtered, washed with methanol and then toluene, to provide 39.1 g of poisoned Raney nickel catalyst.

The hydrogenolysis of 83.1 g of the oily substance obtained in EXAMPLE 1 which contained the polythiobisphenol (corresponding to 81% of 0.6 moles of phenol) was carried out in the same manner as in EXAMPLE 1 at 150° C. for 15 hours with the use of 6.3 g of the above poisoned Raney nickel catalyst, to provide 59.2 g of 4-mercaptophenol, which was found to have 97% purity. Then, the calculated reduction yield was found to be 94%.

EXAMPLE 8

An amount of 83.1 g of the oily substance obtained in EXAMPLE 1 which contained the polythiobisphenol (corresponding to 81% of 0.6 moles of phenol) and 60 g of isopropanol were placed together with the 6.3 g of the poisoned Raney nickel catalyst prepared in EXAMPLE 1 in a 300 ml capacity autoclave. The inside of the autoclave was replaced by nitrogen, and then the nitrogen was replaced by hydrogen of a pressure of 14 kg/cm$^2$. The autoclave was then heated to 150° C. to start the reaction, when the inside was under a pressure of 20 kg/cm$^2$. During the reaction, every time the inside hydrogen pressure decreased to 18 kg/cm$^2$, hydrogen was supplied into the autoclave to pressurize the inside at 20 kg/cm$^2$.

After the reaction at 150° C. for 14 hours, the autoclave was allowed to cool, the pressure inside thereof was released, and the reaction mixture was taken out of the autoclave. The resultant reaction mixture was filtered to remove the catalyst therefrom and then the isopropanol was removed by distillation followed by vacuum distillation to provide 59.8 g of 4-mercaptophenol. By gas chromatographic analysis, the 4-mercaptophenol was found to have 97% purity, and the reduction yield was found to be 94%.

EXAMPLE 9

An amount of 83.1 g of the oily substance obtained in EXAMPLE 1 which contained the polythiobisphenol (corresponding to 81% of 0.6 moles of phenol) and 60 g of dioxane were placed together with 6.3 g of the poisoned Raney nickel catalyst prepared in EXAMPLE 1 in a 300 ml capacity autoclave. The inside of the autoclave was replaced by nitrogen, and then the nitrogen was replaced by hydrogen of a pressure of 12 kg/cm$^2$. The autoclave was then heated to 150° C. to start the reaction, when the inside pressure was 20 kg/cm$^2$. During the reaction, when the inside pressure decreased to 18 kg/cm², hydrogen was supplied into the autoclave to pressurize the inside at 20 kg/cm².

After the reaction at 150° C. for 11 hours, the autoclave was allowed to cool, the pressure inside thereof was released, and the reaction mixture was taken out of the autoclave. The resultant reaction mixture was filtered to remove the catalyst therefrom and then the dioxane was removed by distillation followed by vacuum distillation to provide 60.0 g of 4-mercaptophenol. By gas chromatographic analysis, the 4-mercaptophenol was found to have 97% purity, and the reduction yield was found to be 95%.

EXAMPLE 10

An amount of 0.5 moles of a substituted phenol shown in Table 3 was dissolved in 250 g of a solvent shown in Table 3, and was added thereto 2.5 g of N,N-dialkyl acid amide or 0.05 g of bromine or metal halide shown in Table 3 as a catalyst in the same manner as in EXAMPLE 1.

An amount of 37.1–67.5 g (0.27–0.55 moles) of sulfur monochloride was added dropwise to the above solution, and the reaction was carried out in the same manner as in EXAMPLE 1. After the reaction, the solvent was removed by vacuum distillation to provide an oily substance. This substance was sampled, and was reduced in the same manner as in EXAMPLE 1 to determine the yield of the polythiobisphenol by gas chromatography. The results are shown in Table 3.

An amount of the above oily substance which contained polythiobisphenol corresponding to 0.4 to 0.6 moles of phenol and 60 g of toluene were placed together with 6.3 g of poisoned Raney nickel catalyst or 5.3 g of nickel/diatomaceous earth in a 300 ml capacity autoclave, and the hydrogenolysis of the polythiobisphenol was carried out at a temperature of 150° C. for 8–12 hours in the same manner as in EXAMPLE 1.

EXAMPLE 11

An amount of 0.2 moles of a substituted phenol shown in Table 4 was dissolved in 100 g of ethylglycol acetate or ethyl acetate, and was added thereto 2 g of N,N-dimethylformamide or 0.02 g of bromine in the same manner as in EXAMPLE 1.

The reaction was carried out in the same manner as in EXAMPLE 1 by adding 14.9 g (0.11 mole) of sulfur monochloride to the above solution. After the reaction, the solvent was removed by distillation from the reaction mixture.

To the thus obtained oily substance which contained polythiobisphenol was added 80 g of toluene to dissolve the polythiobisphenol therein by the application of heat thereto. An amount of 10 g (0.15 mole) of zinc powder and 35 g (0.34 mole) of 35% hydrochloric acid were added to the solution to effect the quantitative reduction of the polythiobisphenol. After the reaction, the organic layer was separated from the reaction mixture, made neutral, and washed with water. The toluene was removed by distillation from the organic layer, and then the vacuum distillation of the residue provided the reduction products, i.e., the corresponding mercaptophenols.

The mercaptophenol was subjected to qantitative analysis by gas chromatography to determine the purity thereof and the reduction yield. The results are shown in Table 4.

EXAMPLE 12

Dithiobisphenol was prepared according to the method of Z. S. Ariyan et al. (J. Chem. Soc., 3876 (1962)). An amount of 50.1 g (0.2 mole) of the dithiobisphenol, 60 g of toluene and 5.3 g of nickel/diatomaceous earth catalyst were placed in an autoclave, and the reaction was carried out at 150° C. for 8 hours in the

TABLE 3

| Phenols | Solvents[1] | Catalysts | Moles of $S_2Cl_2$ | Yields of Polythiobisphenols (%) | Nickel Catalysts[2] | Mercaptophenols Purity[3] (%) | Reduction Yields (%) | Bp. (°C.) |
| --- | --- | --- | --- | --- | --- | --- | --- | --- |
| m-cresol | EGA | DMA | 0.27 | 78 | I | a 96 | 96 | 119–121/5 mmHg |
| m-cresol | ethyl acetate | LiI | 0.27 | 74 | II | a 95 | 95 | 118–121/5 mmHg |
| 2,6-xylenol | EGA | DMA | 0.27 | 84 | II | b 96 | 95 | 121–123/5 mmHg |
| 2,6-xylenol | ethyl acetate | LiBr | 0.27 | 78 | I | b 93 | 95 | 119–123/5 mmHg |
| 2,6-diisopropyl-phenol | EGA | DMF | 0.41 | 90 | II | c 98 | 95 | 118–120/5 mmHg |
| 2,6-di-tertiary butylphenol | ethyl acetate | bromine | 0.55 | 88 | II | d 97 | 94 | 125–127/1 mmHg |
| 2,4-xylenol | EGA | bromine | 0.27 | 72 | II | e 92 | 95 | 92–98/5 mmHg |

[1]EGA: ethylglycol acetate
[2]I: poisoned Raney nickel
II: nickel/diatomaceous earth
[3]a: 4-mercapto-m-cresol
b: 4-mercapto-2,6-xylenol
c: 4-mercapto-2,6-diisopropylphenol
d: 4-mercapto-2,6-di-tertiary butylphenol
e: 6-mercapto-2,4-xylenol The toluene was removed by distillation followed by vacuum distillation provided mercaptophenols.

The purity of the thus obtained mercaptophenols and the reduction yield calculated as hereinbefore were shown in Table 3.

same manner as in EXAMPLE 1. After the reaction, toluene was removed from the reaction mixture followed by vacuum distillation provided 4-mercaptophenol. By gas chromatographic analysis, the 4-mercaptophenol was found to have a purity of 98%, and the reduction yield was found to be 98%.

TABLE 4

| Phenols | Solvents[1] | Catalysts | Moles of $S_2Cl_2$ | Products Mercaptophenols[2] | Purity (%) | Yields (%) | Bp. (°C.) |
|---|---|---|---|---|---|---|---|
| o-fluorophenol | EGA | DMF | 0.11 | a | 97 | 72 | 98–100/5 mmHg |
| o-fluorophenol | ethyl acetate | bromine | 0.11 | a | 95 | 69 | 98–100/5 mmHg |
| 2-chlorophenol | EGA | DMF | 0.11 | b | 97 | 71 | 95–97/5 mmHg |

[1]EGA: ethylglycol acetate
[2]a: 2-hydroxy-5-fluorothiophenol
b: 2-hydroxy-5-chlorothiophenol

What is claimed is:

1. A process for producing polythiobisphenols which comprises: reacting a phenol having the formula

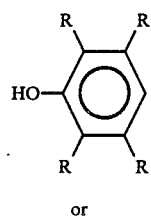

or

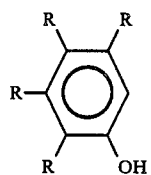

wherein each R independently represents a hydrogen, a halogen or an alkyl, with sulfur monochloride in a polar organic solvent in the presence of a nitrogen-containing organic compound as a catalyst which is selected from the group consisting of tertiary amines which are selected from the group consisting of trimethylamine, triethylamine, triethylenediamine and tetramethylethylenediamine; quaternary ammonium halides which are selected from the group consisting of a trialkylaryl ammonium halide and a tetraalkyl ammonium halide; and heteroaromatic compounds which are selected from the group consisting of pyridine, 2-chloropyridine, α-picoline and β-picoline, in an amount of 1–30% by weight based on the phenol used, thereby to produce the polythiobisphenol having the formula

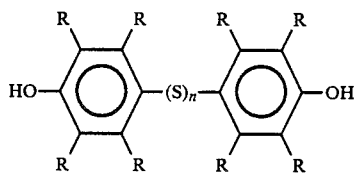

or

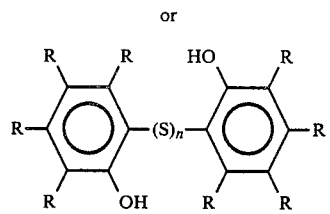

wherein R is the same as above, and n is an integer of 2–4.

2. The process as claimed in claim 1 wherein the trialkylaryl ammonium halide is triethylbenzyl ammonium chloride.

3. The process as claimed in claim 1 wherein the tetraalkyl ammonium halide is tetraethyl ammonium chloride.

4. The process as claimed in claim 1 wherein the catalyst is used in amounts of about 2–20% by weight based on the amount of the phenol used.

5. The process as claimed in claim 1 wherein the catalyst is used in amounts of 3–12% by weight based on the amount of the phenol used.

6. The process as claimed in claim 1 wherein each R is a hydrogen.

7. The process as claimed in claim 1 wherein the polythiobisphenol is di-, tri- or both di- and trithiobisphenol.

8. The process as claimed as claim 1 wherein the reaction is carried out at temperatures of about from −20° C. to 50° C.

9. The process as claimed in claim 1 wherein the organic polar solvent is used in amounts of about 2 to 10 times as much as the weight of the phenol used.

10. The process as claimed in claim 1 wherein the organic polar solvent is used in amounts of about 3 to 8 times as much as the weight of the phenol used.

11. A process for producing polythiobisphenols which comprises: reacting a phenol having the formula

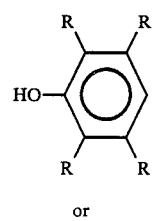

or

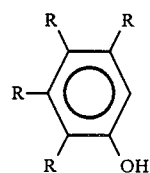

wherein each R independently represents a hydrogen, a halogen or an alkyl, with sulfur monochloride in a polar organic solvent in the presence of an alkylated acid amide which is selected from the group consisting of N,N-dialkylformamides and N,N-dialkylacetamides, in amounts of 2–20% by weight based on the phenol used, thereby to produce the polythiobisphenol having the formula

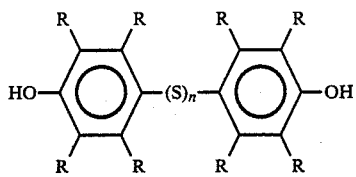 (III)

or

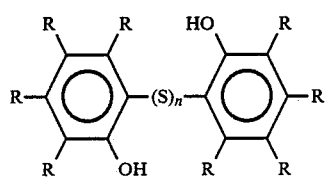 (IV)

wherein R is the same as above, and n is an integer of 2–4.

12. The process as claimed in 11 wherein the N,N-dialkylformamide is N,N-dimethylformamide.

13. The process as claimed in 11 wherein the N,N-dialkylacetamide is N,N-dimethylacetamide.

14. The process as claimed in claim 11 wherein the catalyst is used in amounts of about 3–12% by weight based on the amount of the phenol used.

15. The process as claimed in 11 wherein each R is a hydrogen.

16. The process as claimed in claim 11 wherein the polythiobisphenol is di-, tri- or both di- and trithiobisphenol.

17. The process as claimed in claim 11 wherein the reaction is carried out at temperatures of about from −20° C. to 50° C.

18. The process as claimed in claim 11 wherein the organic polar solvent is used in amounts of about 2 to 10 times as much as the weight of the phenol used.

19. The process as claimed in claim 18 wherein the organic polar solvent is used in amounts of about 3 to 8 times as much as the weight of the phenol used.

20. The process for producing polythiobisphenols which comprises: reacting a phenol having the formula

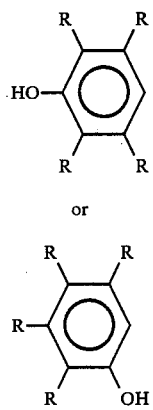

wherein each R independently represents a hydrogen, a halogen or an alkyl, with sulfur monochloride in a polar organic solvent in the presence of an alkali metal halide, in amounts of about 200–2000 ppm based on the amount of sulfur monochloride, thereby to provide the polythiobisphenol having the formula

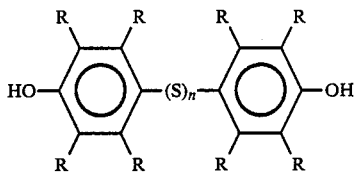 (III)

or

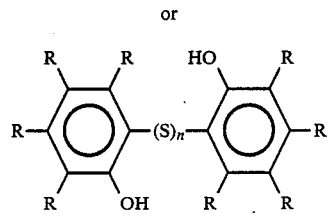 (IV)

wherein R is the same as above, and n is an integer of 2–4.

21. The process as claimed in claim 20 wherein the alkali metal halide is selected from the group consisting of lithium halide, sodium halide, and potassium halide.

22. The process claimed in claim 20 wherein each R is a hydrogen.

23. The process as claimed in claim 20 wherein the polythiobisphenol is di-, tri- or both di- and trithiobisphenol.

24. The process as claimed in claim 20 wherein the reaction is carried out at temperatures of about −20° C. to 50° C.

25. The process as claimed in claim 20 wherein the organic polar solvent is used in amounts of about 2 to 10 times as much as the weight of the phenol used.

26. The process as claimed in claim 25 wherein the organic polar solvent is used in amounts of about 3 to 8 times as much as the weight of the phenol used.

27. A process for producing mercaptophenols which comprises:
reducing polythiobisphenols having the formula

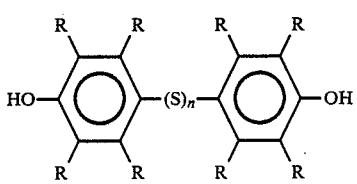 (III)

or

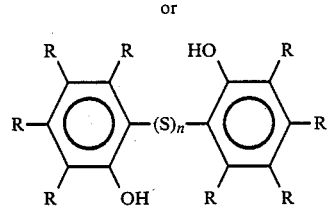 (IV)

wherein each R independently represents a hydrogen or an alkyl, and n is an integer of 2–4, with hydrogen in the presence of a Raney nickel catalyst which is in advance poisoned by heating in the absence of hydrogen in a liquid organosulfur compound which is selected from the group consisting of an aliphatic mercaptane, an aliphatic mercaptoalcohol, an aromatic mercaptane and a heteroaromatic sulfur compound which is selected from the group consisting of thiophene, 2-methylthiophene and 4-methylthiophene, thereby to provide the mercaptophenol having the formula

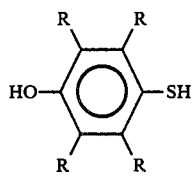

or

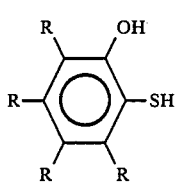

wherein R is the same as above.

28. The process as claimed in claim 27 wherein the aliphatic mercaptane is octyl mercaptane.

29. The process as claimed in claim 27 wherein the aliphatic mercaptoalcohol is 2-mercaptoethanol.

30. The process as claimed in claim 27 wherein the aromatic mercaptane is thiophenol, 2-mercaptophenol or 4-mercaptophenol.

31. The process as claimed in claim 27 wherein the nickel catalyst is used in amounts of about 1–30% by weight based on the amount of the polythiobisphenol.

32. The process as claimed in claim 27 wherein the nickel catalyst is used in amounts of about 5–10% by weight based on the amount of the polythiobisphenol.

33. The process as claimed in claim 27 wherein each R is a hydrogen.

34. The process as claimed in claim 27 wherein the polythiobisphenol is a di-, tri-, or both di- and trithiobisphenol.

35. The process as claimed in claim 27 wherein the reaction is carried out in an aromatic hydrocarbon.

36. A process for producing mercaptophenols which comprises:
(a) reacting a phenol having the formula

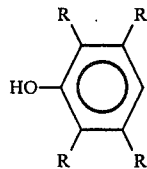

or

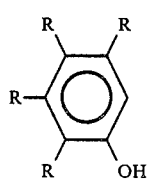

wherein each R independently represents a hydrogen, a halogen or an alkyl, with sulfur monochloride in a polar organic solvent
(i) in the presence of a nitrogen-containing organic compound as a catalyst which is selected from the group consisting of tertiary amines which are selected from the group consisting of trimethylamine, triethylamine, triethylenediamine and tetramethylethylenediamine; quaternary ammonium halides which are selected from the group consisting of a trialkylaryl ammonium halide and a tetraalkyl ammonium halide; and heteroaromatic compounds which are selected from the group consisting of pyridine, 2-chloropyridine, α-picoline and β-picoline, in an amount of 1–30% by weight based on the phenol used, or
(ii) in the presence of an alkylated acid amide which is selected from the group consisting of N,N-dialkylformamides and N,N-dialkylacetamides, in amounts of 2–20% by weight based on the phenol used, or
(iii) in the presence of an alkali metal halide in amounts of about 200–2000 ppm based on the amount of sulfur monochloride used,
thereby to provide polythiobisphenols having the formula

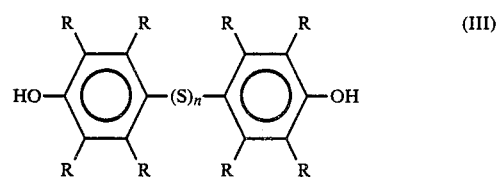

or

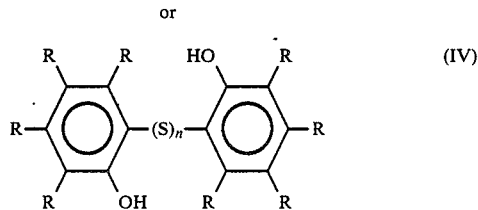

wherein each R is the same as above, and n is an integer of 2–4;
(b) reducing the polythiobisphenol with hydrogen in the presence of a nickel catalyst.

37. The process as claimed in claim 36 wherein the trialkylaryl ammonium halide is triethylbenzyl ammonium chloride.

38. The process as claimed in claim 36 wherein the tetraalkyl ammonium halide is tetraethyl ammonium chloride.

39. The process as claimed in claim 36 wherein the N,N-dialkylformamide is N,N-dimethylformamide.

40. The process as claimed in claim 36 wherein the N,N-dialkylacetamide is N,N-dimethylacetamide.

41. The process as claimed in claim 36 wherein the nitrogen-containing organic compound is used in amounts of about 2–20% by weight based on the amount of the phenol used.

42. The process as claimed in claim 36 wherein the nitrogen-containing organic compound is used in amounts of about 3–12% by weight based on the amount of the phenol used.

43. The process as claimed in claim 36 wherein the alkylated acid amide is used in amounts of about 3–12% by weight based on the amount of phenol used.

44. The process as claimed in claim 36 wherein each R is a hydrogen.

45. The process as claimed in claim 36 wherein the polythiobisphenol is di-, tri-, or both di- and trithiobisphenol.

46. The process as claimed in claim 36 wherein the reaction of phenol with sulfur monochloride is carried out at temperatures of about from −20° C. to 50° C.

47. The process as claimed in claim 36 wherein the nickel catalyst is Raney nickel.

48. The process as claimed in claim 36 wherein the nickel catalyst comprises nickel supported on diatomaceous earth.

49. The process as claimed in claim 36 wherein the Raney nickel catalyst is in advance poisoned by heating in the absence of hydrogen in a liquid organosulfur compound which is selected from the group consisting of an aliphatic mercaptane, an aliphatic mercaptoalcohol, an aromatic mercaptane and a heteroaromatic sulfur compound which is selected from the group consisting of thiophene, 2-methylthiophene and 4-methylthiophene.

50. The process as claimed in claim 49 wherein the aliphatic mercaptane is octyl mercaptane.

51. The process as claimed in claim 49 wherein the aliphatic mercaptoalcohol is 2-mercaptoethanol.

52. The process as claimed in claim 49 wherein the aromatic mercaptane is thiophenol, 2-mercaptophenol or 4-mercaptophenol.

53. The process as claimed in claim 49 wherein the nickel catalyst is used in amounts of about 5–10% by weight based on the amount of polythiobisphenol.

54. The process as claimed in claim 49 wherein the alkali metal halide is selected from the group consisting of lithium halide, sodium halide and potassium halide.

55. The process as claimed in claim 49 wherein the reduction reaction of polythiobisphenol is carried out in an aromatic hydrocarbon.

* * * * *